United States Patent [19]

Price

[11] Patent Number: 4,489,052
[45] Date of Patent: Dec. 18, 1984

[54] QUANTITATIVE AUTORADIOGRAPHIC MAPPING OF FOCAL HERPES SIMPLEX VIRUS ENCEPHALITIS USING A RADIOLABELED ANTIVIRAL DRUG

[75] Inventor: Richard Price, Scarsdale, N.Y.

[73] Assignee: Sloan-Kettering for Cancer Research, New York, N.Y.

[21] Appl. No.: 418,156

[22] Filed: Sep. 15, 1982

[51] Int. Cl.³ .................... A61K 43/00; A61K 49/00
[52] U.S. Cl. .................................... 424/1.1; 424/9; 536/23
[58] Field of Search ................ 424/1.1, 9; 536/23

[56] References Cited

U.S. PATENT DOCUMENTS 4,341,754  7/1982  Kaplan et al. .................... 424/1

OTHER PUBLICATIONS

Fong et al., J. of Virology, vol. 34, (1980), 644–649.
Tuckes et al., Chem. Abstracts, vol. 95 (1981), #86254g.
Boorstein et al., Chem. Abstracts, vol. 98 (1983), #194521n.
Dundarov et al., Chem. Abstracts, vol. 76 (1972), #23591b.
Machida et al., Antimicrob. Agents Chemother., vol. 17 (1980), 109–114.
Saito et al., Science, vol. 217 (1982), 1151–1153.

*Primary Examiner*—Christine M. Nucker
*Attorney, Agent, or Firm*—Felfe & Lynch

[57] ABSTRACT

A method of mapping herpes simplex viral infection comprising administering a radiolabeled antiviral active 5-substituted 1-(2'-deoxy-2'-substituted-D-arabinofuranosyl) pyrimidine nucleoside to the infected subject, and scanning the area in which the infection is to be mapped for the radiolabel.

5 Claims, No Drawings

QUANTITATIVE AUTORADIOGRAPHIC MAPPING OF FOCAL HERPES SIMPLEX VIRUS ENCEPHALITIS USING A RADIOLABELED ANTIVIRAL DRUG

This invention was made with Government support under USPHS grants NS 12396 and CA-18601. The Government has certain rights in this invention.

BACKGROUND

HSV type 1 is a major cause of severe sporadic encephalitis in man. The epidemiology, clinical presentation, natural history, pathology and treatment of this disorder are characterized in the literature. The early symptoms and signs of HSV encephalitis, including personality change, behavioral disturbance, seizures and mutism, are anatomically explained by the predilection for the infectious process to involve early the medial temporal lobe, orbital frontal lobe and other "limbic" areas of the brain. Although late in the disease, destruction of these and other areas readily explains the severe sequelae in survivors, early in the illness, when diagnosis and institution of therapy are of paramount importance, symptoms and signs may be due to reversible physiological disturbance. It is on this phase of infection that the present invention is directed. For it is during this phase that conversion of a limited number of cells to virus-directed metabolism, in concert with secondary host responses, may lead to breakdown in the integrated reception, conduction and transmission of neural signals, not only in the immediate focus of infection, but beyond, within anatomically and functionally related regions of brain, resulting in the production of negative (loss of function) or positive (seizures) neurological manifestations.

A major impediment to effective management of HSV encephalitis is the lack of a reliable, non-invasive test which will allow early diagnosis. Unfortunately, present neurodiagnostic studies such as CT and radionuclide scanning may yield normal results early in the disease while viral serology is only retrospectively useful, and even then may not be definitive. At present, brain biopsy is the only definitive means of early diagnosis and this can cause brain damage in its use. Because of the drawbacks of known diagnostic methods, the clinician is left with a difficult decision which may result in delayed or inappropriate therapy. Clearly there is a need for an improved non-invasive diagnostic method such as provided by this invention.

The development of genuinely effective therapy for HSV encephalitis has made a non-invasive early diagnostic method even more useful than before such treatment was available. Thus, because the demonstration by the NIAID Collaborative Study that ara-A is less than optimal, newer, potentially more effective, drugs are currently being developed and tested including several drugs which exploit the virus-coded thymidine kinase (TK) and DNA polymerase enzymes to achieve specificity of antiviral effect. These include the very effective anti-viral pyrimidine nucleoside compounds disclosed in U.S. Pat. No. 4,211,773 to Lopez et al (see also Lopez et al. *Antimicrob Agents Chemother* 17: 803–806 (1980); Fox, J.J. et al. In *Medicinal Chemistry Advances,* FG DELAS HERAS, S VEGA (Eds), Pergamon Press, Elmsford, NY, p. 27–40 (1981); Watanabe et al. *J MED. CHEM* 22: 21–24, (1979). The availability of such new therapies renders early diagnosis all the more pressing since the stage of disease at which therapy is instituted appears very likely to determine the quality of outcome.

The present invention provides a non-invasive, accurate diagnostic test for HSV-1 encephalitis.

DESCRIPTION

The selective uptake by infected cells of an antiviral drug which serves as substrate for virus-coded thymidine kinase (TK) is to be exploited by the present invention for diagnostic methods. An experimental foundation for this invention was carried out using an animal model of HSV-1 encephalitis. Using radiolabeled antiviral agents, and quantitative autoradiography, selective in vivo uptake within HSV-1 infected brain regions of a rat allowed mapping viral infected tissue. After penetration into the brain, this labeled antiviral agent is selectively phosphorylated by viral TK expressed in infected cells. The metabolic products (nucleotides and perhaps DNA) "trapped" within these cells were assessed quantitatively in autoradiograms of brain sections permitting mapping of the infected cells.

Especially preferred are the antiviral pyrimidine nucleoside compounds disclosed in U.S. Pat. No. 4,211,773, which can be radiolabeled by various procedures depending on the label used. Mapping techniques will depend on the radiolabel as well. Thus, if a fluorine (such as $^{18}F$) or bromine (such as $^{76}Br$ or $^{77}Br$) label is used, PET (position emission tomography) can be used. Iodine labeling (e.g., $^{131}I$ or $^{127}I$) will permit more generally available gamma scanning apparatus and techniques to be applied.

A general view of the technique of quantitative autoradiography to assess regional cerebral metabolism including detailed descriptions of the 2-DG method by Sokoloff which discuss the theoretical and technical aspects of such studies as well as the directions of current investigations is found e.g. in Sokoloff, *J. Cereb. Blood Flow Metab* 1: 7–36 (1981); Sokoloff, *Neurosci Res Prog. Bull.* 19: 154–210 (1981).

EXPERIMENTAL

The following laboratory animal experiments were carried out to show that infected regions do indeed selectively sequester and concentrate labeled anti-viral agents and that these regions can be mapped autoradiographically. In this sense, quantitative autoradiography can be considered the analog in the small experimental animal of in vivo radionuclide imaging techniques to be applied to man. The study is also useful in that it allows one to follow the path of HSV infection in the brain so that the disease can be studied.

Focal encephalitis was produced in 150–200 gm female CD rats (Charles River Laboratories) by intraocular (i.o.) inoculation of the right eye with $2.6 \times 10^6$ plaque-forming units of the F-strain of HSV-1 suspended in a volume of 20 $\mu$l (8). The i.o. route was chosen because it avoids the need for direct intracerebral injection with attentent trauma and because a reproducible, anatomically stereotyped focal encephalitis ensues (9). In some experiments, rats were immunosuppressed by intraperitoneal injection of 250 mg/kg of cyclophosphamide administered one day after viral challenge in order to produce more severe brain infection. Rats were sacrificed for study on day 5 or 6 after viral inoculation. Five mg/kg of $^{14}C$-FMAU (labeled at the number 2 position of the pyrimidine ring) with a specific activity of 47.5 $\mu$Ci/mg (12.3 nCi/nM) was injected intravenously (10). Three rats were injected with the isotope 24 hours before sacrifice, while in the remainder, 6 hours elapsed between injection and sacrifice. In the case of animals sacrificed at 6 hours, frequent arterial plasma samples were analyzed for $^{14}C$ activity by liquid scintillation counting; in addition, arterial blood pressure was monitored continuously and arterial blood gases were sampled intermittently via femoral cannulae. Previous studies have shown that in the rat most FMAU is excreted unchanged in the urine and only a minor fraction undergoes metabolic alteration (11). Animals were sacrificed by injection of a lethal dose of pentobarbital (42 mg) and their brains removed rapidly, frozen in Freon (cooled to $-40°$ C. in dry ice) within 2-3 minutes of death, and stored at $-70°$ C. Cyrostat-cut 20-micron coronal brain sections were prepared for $^{14}C$ quantitative autoradiography using MR-1 (Kodak) film employing methods described by Sokoloff et al (7). In addition to quadruplicate serial brain sections (taken at 30-section intervals), sections of eye, liver and skeletal muscle along with a series of eleven $^{14}C$-methylmethacrylate standards (Amersham) were included on each film. Tissue sections immediately adjacent to those selected for autoradiography were processed for peroxidase-antiperoxidase (PAP) staining of HSV-1 antigens, as previously described (12). Autoradiographic images were digitized by means of a Vidicon-based EyeCom 11 image-processing system linked to a PDP 11/23 microcomputer. Optical density in user-defined brain regions of interest was then converted to $^{14}C$ activity concentration (nCi/gm) using a calibration curve derived from analysis of the $^{14}C$ standards.

These initial studies reflect observations on ten rats receiving $^{14}C$-FMAU. Seven of these were infected, and three uninfected control rats were subjected to a cortical freeze lesion (13) to test the effects of necrosis and breakdown of the blood-brain barrier on drug distribution. In autoradiograms prepared from each HSV-1-infected rat, $^{14}C$ activity exceeded background within infected regions and correlating closely with viral antigen staining in each case. Data from a representative animal studied 6 hours after $^{14}C$-FMAU injection are given in Table 1. It was observed that the plasma $^{14}C$-FMAU concentration fell rapidly over the first 30 mins and more slowly thereafter to a final concentration of approximately 185 nCi/gm at the time of sacrifice. The derived data in Table 1, show that the background distribution of $^{14}C$ activity was quite uniform, with only minor variations among uninfected brain regions. In contrast, within infected structures (including the retina, optic chiasm, suprachiasmatic nuclei of the hypothalamus, left optic tract, left thalamus, central mesencephalon and pineal gland) activity was consistently increased, ranging from 2 to more than 13 times that of background. The intensity of uptake appeared to vary with the density of infected cells and stage of viral replication within each of these areas. In the choroid plexus, $^{14}C$ activity was similar to that of blood and liver, and represented the only uninfected region exhibiting activity above that of background brain. In the other infected animals studied, a similar correlation between $^{14}C$-FMAU uptake and regional infection as defined by PAP staining was found, with infected-to-background-brain activity ratios being of a similar magnitude. In animals sacrificed 24 hours after isotope injection, isotope uptake was similarly enhanced within infected brain regions and contrasted with the low activity of background uninfected brain, with the exception of the lateral walls of the lateral ventricles where higher activity was noted apparently within the uninfected ependymal lining. In the three animals subjected to cortical freeze lesions, no increase in isotope uptake was detected in or surrounding the area of necrosis, indicating that increased local drug concentration was not merely a result of altered blood-brain barrier permeability.

Our results demonstrate that radiolabeled FMAU is selectively taken up by infected brain cells and that this tracer can be used to map the distribution of HSV-1 infection. Quantitative autoradiography, which permits measurement of radiolabeled drug uptake by a limited number of infected cells, should prove valuable in studies of the metabolism of this and related drugs whose mechanism of action involves phosphorylation by viral TK. In this regard quantitative autoradiography is superior to liquid scintillation counting of organ lysates for the assessment of labeled drug uptake, since with the latter technique high uptake by a small number of cells is likely to be masked by the large volume of background activity associated with uninfected brain.

To apply these results for diagnostic purposes to map infected brain in a subject we will employ a scanning technique for imaging radioactive tracer distribution in vivo. This will be used to detect human HSV encephalitis. We will use not only FMAU but also the related iodine containing potent antiviral pyrimidine nucleodise 2'-fluoro-5-iodo-1-B-D-arabinosylcytosine (FIAC) with the objective that the incorporation of a positron- or gamma-emitting isotope into FIAC be exploited by position emission or single photon tomography (PET), or perhaps even by clinical gamma scanning, to image brain infection in man. In fact, it is expected that the class of antiviral pyrimidine nucleosides disclosed in U.S. Pat. No. 4,211,773, when labeled for the scanning technique to be used, can be used to practice the invention.

Examples of various labeled 5-substituted 1-(2'-deoxy-2'-substituted-beta-D-arabinofuranosyl pyrimidine nucleosides compounds which may be prepared in accordance with procedures such as disclosed in U.S. Pat. No. 4,211,773 wherein the non-labeled compounds are claimed, include compounds such as

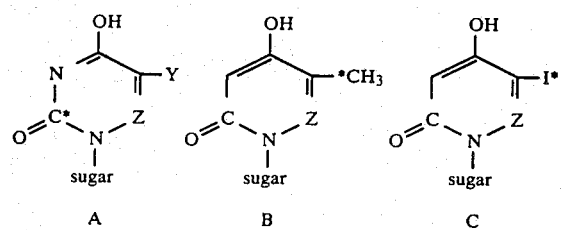

Carbon 14 and Iodine 125 are two labels useful for gamma scanning techniques. $^{14}C$-FMAU used in the above test corresponds to formula A with respect to position of labeling. It is expected that, for convenience and safety of the workers synthesizing these compounds, labeled compounds corresponding to tagged (*) position in formula B will be preferred as the compound without -$^{14}CH_3$ can be prepared and the labeled methyl added in the last step. This has the further advantage of minimizing the amount of (expensive) labeled methyl required to obtain a given amount of product, by reducing loses during synthesis. Such a preparation procedure also greatly expedites the possible use of short lived isotopes, e.g. 11 C in a PET mapping procedure, with its reduced risk to the patient from radiation from the tagged material.

Iodinated compounds can be used, such as exemplified by formula C. Thus, for example, FIAC can be prepared in accordance with the procedures in U.S. Pat. No. 4,211,773 and then permitted to equilibrate with Iodine 125.

It will be understood that the specification and examples are illustrative but not limitative of the present invention and that other embodiments within the spirit and scope of the invention will suggest themselves to those skilled in the art.

TABLE 1

Regional tissue $^{14}$C concentrations in an HSV-1-infected rat receiving $^{14}$C-FMAU 6 hours before sacrifice. Eye and brain section data are derived from digitized autoradiograms shown in FIG. 2.

| Tissue Region of Interest | Area[1] (pixels) | Viral Antigen Staining[2] | $^{14}$C Radioactivity Concentration (nCi/gm ± SD) |
|---|---|---|---|
| Liver | 3395 | — | 188.25 ± 13.19 |
| Eye (B)[3] | | | |
| Retina, posterior | 45 | + | 2447.81 ± 172.66 |
| Retina, inferior | 49 | + | 1528.07 ± 140.36 |
| Brain (C) | | | |
| Background, left cortex | 621 | — | 104.35 ± 4.88 |
| Left ventricular choroid plexus | 27 | — | 188.59 ± 9.18 |
| Optic chiasm, right | 15 | + | 325.12 ± 16.46 |
| Brain (D) | | | |
| Background, left cortex | 1221 | — | 95.29 ± 4.32 |
| Left hypothalamus | 33 | + | 1170.91 ± 66.90 |
| Right hypothalamus | 27 | + | 1138.10 ± 99.57 |
| Left optic tract | 9 | + | 1105.89 ± 77.34 |
| Brain (E) | | | |
| Background, left cortex | 441 | — | 96.78 ± 4.66 |
| Background, right central thalamus | 441 | — | 67.47 ± 3.90 |
| Left dorsomedial thalamus | 35 | + | 1183.53 ± 163.31 |
| Left lateral thalamus | 15 | + | 198.21 ± 21.00 |
| Brain (F) | | | |
| Background, left cortex | 775 | — | 106.57 ± 5.53 |
| Central midbrain | 45 | + | 468.81 ± 23.96 |
| Brain (G) | | | |
| Background, left cortex | 1287 | — | 83.08 ± 7.70 |
| Background, central brainstem | 1287 | — | 110.97 ± 9.98 |
| Pineal gland | 63 | + | 1509.18 ± 97.65 |

[1]Area of the user-defined region of interest assessed in the digitized autoradiogram
[2]PAP staining of viral antigens in the adjacent serial section
[3]Letter designations in parentheses refer to digitized autoradiograms shown in FIG. 2

REFERENCES AND NOTES

7. L. Sokoloff, M. Reivich, C. Kennedy, M. H. Des Rosiers, C. S. Patlak, K. D. Pettigrew, O. Sakurada and M. Shinohara, *J. Neurochem.* 28, 897 (1977). L. Sokoloff, *J. Cereb. Blood Flow Metab.* 1, 7 (1981).
8. R. W. Price and J. Schmitz, *Infect. Immun.* 19, 523 (1978).
9. Infection in this model spreads along neural pathways. Characteristically, infection is most prominent in the visual pathway of the inoculated eye, i.e. the right optic nerve and the left optic tract along with their target nuclei, including the suprachiasmatic nuclei bilaterally, the left lateral geniculate body and the left superior colliculus. Infection at times also involves the pineal gland (via the postganglionic fibers of the superior cervical ganglion), the central mesencephalon and the descending trigeminal tract. Y. Saito and R. W. Price, *Trans. Amer. Neurol. Asso.* (in press).
10. [2-$^{14}$C]FMAU was synthesized and its purity assessed in the Laboratory of Organic Chemistry of Sloan-Kettering Institute. T-L. Su, K. A. Watanabe and J. J. Fox (to be published).
11. The distribution of $^{14}$C-FMAU in tissues of uninfected rats has been studied extensively, and the dosage and timing of our study was based upon these observations. T-C. Chou, A. Feinberg and F. S. Philips (unpublished).
12. R. W. Price, R. Rubenstein, T. H. Joh and D. J. Reis, *Brain Res.* 214, 357 (1981).
13. R. G. Blasberg, J. Gazendam, C. S. Patlak, J. D. Fenstermacher in *Advances in Neurology*, Vol. 28, *Brain Edema.* J. Cervos-Navarro and R. Ferszt, Eds. (Raven, New York, 1980), p. 255.

What is claimed is:
1. Method of mapping herpes simplex viral infection comprising administering a radiolabeled antiviral active 5-substituted
   1-(2'-deoxy-2'-substituted-D-arabinofuranosyl) pyrimidine nucleoside to the infected subject, and scanning the area in which the infection is to be mapped for the radiolabel.
2. The method of claim 1 wherein scanning is accomplished by gamma scanning apparatus.
3. The method of claim 2 wherein the radiolabel is an isotope selected from the group consisting of $^{131}$I and $^{127}$I.
4. The method of claim 1 wherein scanning is accomplished using a positron emission tomography technique.
5. The method of claim 4 wherein the radiolabel is an isotope selected from the group consisting of $^{11}$C, $^{14}$C, $^{18}$F, $^{76}$Br and $^{77}$Br.

* * * * *